United States Patent [19]

Perkins

[11] Patent Number: 5,005,570
[45] Date of Patent: Apr. 9, 1991

[54] METHOD AND MEANS FOR DISPENSING RESPIRATING GASES BY EFFECTING A KNOWN DISPLACEMENT

[76] Inventor: Warren E. Perkins, 9960 S A-1-A, Apt. 1901, Jensen Beach, Fla. 34957

[21] Appl. No.: 416,511

[22] Filed: Oct. 3, 1989

Related U.S. Application Data

[60] Division of Ser. No. 112,117, Oct. 25, 1987, Pat. No. 4,873,971, which is a continuation-in-part of Ser. No. 783,121, Oct. 2, 1985, Pat. No. 4,705,034.

[51] Int. Cl.[5] .................... A62B 17/04; A62B 18/00; A62B 7/00; A61M 16/00
[52] U.S. Cl. ........................... 128/204.23; 128/204.21; 128/204.24
[58] Field of Search ...................... 128/204.21, 204.26, 128/205.18, 201.23, 204.24, 204.23, 204.25, 205.13, 205.16, 205.14, 205.24, 204.29; 222/249, 250, 251

[56] References Cited

U.S. PATENT DOCUMENTS

| 2,755,966 | 7/1956 | Lindars | 222/250 |
|---|---|---|---|
| 2,881,959 | 4/1959 | Sheen | 222/250 |
| 3,208,644 | 9/1965 | Bergson | 222/249 |
| 3,235,136 | 2/1966 | Fullman | 222/250 |
| 3,292,824 | 12/1966 | Arp et al. | 222/250 |
| 3,357,428 | 12/1967 | Carlson | 128/204.23 |
| 3,522,816 | 8/1970 | Springer | 128/204.24 |
| 3,827,432 | 8/1974 | Lundgren et al. | 128/205.17 |
| 3,910,270 | 10/1975 | Stewart | 128/204.24 |
| 4,036,221 | 7/1977 | Hillsman et al. | 128/204.23 |
| 4,054,133 | 10/1977 | Myers | 128/142.2 |
| 4,096,875 | 6/1978 | Jone et al. | 128/204.24 |
| 4,141,356 | 2/1979 | Smargiassi | 128/204.23 |
| 4,215,409 | 7/1980 | Strowe | 128/204.22 |
| 4,232,668 | 11/1980 | Struport | 128/204.24 |
| 4,278,110 | 7/1981 | Price et al. | 128/204.26 |
| 4,279,360 | 7/1981 | Hauser | 222/250 |
| 4,340,044 | 7/1982 | Levy et al. | 128/204.21 |
| 4,381,002 | 4/1983 | Mon | 128/204.24 |
| 4,414,982 | 11/1983 | Durkan | 128/204.24 |
| 4,457,303 | 7/1984 | Durkan | 128/204.24 |
| 4,461,293 | 7/1984 | Chen | 128/204.24 |
| 4,462,398 | 7/1984 | Durkan et al. | 128/204.24 |
| 4,506,666 | 3/1985 | Durkan | 128/204.24 |
| 4,519,387 | 5/1985 | Durkan et al. | 128/204.26 |
| 4,542,740 | 9/1985 | Kleinschmidt et al. | 128/204.21 |
| 4,570,631 | 2/1986 | Durkan | 128/204.23 |
| 4,651,730 | 3/1987 | von dem Hagen et al. | 128/204.21 |
| 4,665,911 | 5/1987 | Williams et al. | 128/204.21 |
| 4,677,975 | 7/1987 | Edgar et al. | 128/204.23 |
| 4,705,034 | 11/1987 | Perkins | 128/204.26 |

FOREIGN PATENT DOCUMENTS

| 2412328 | 9/1974 | Fed. Rep. of Germany | 128/205.14 |
|---|---|---|---|
| 2435855 | 2/1975 | Fed. Rep. of Germany | 128/240.24 |
| 1936680 | 5/1976 | Fed. Rep. of Germany | 128/204.21 |

OTHER PUBLICATIONS

Auerback et al, "A New Oxygen Cannula System Using Intermittent Demand Nasal Flow", 7/1/78, pp. 39–44.

Primary Examiner—Clifford D. Crowder
Assistant Examiner—Kimberly L. Asher
Attorney, Agent, or Firm—Roland H. Shubert

[57] ABSTRACT

A device for administering oxygen or other respirating gases to a patient premeters and temporarily stores single dose quantities of respirating gas and dispenses each dose in synchronization with the patient's inspiratory cycle. A sensor produces a signal upon the onset of each inhalation and those signals cause single doses of gas to be dispensed to the patient in unison with the patient's respiration cycle.

14 Claims, 4 Drawing Sheets

METHOD AND MEANS FOR DISPENSING RESPIRATING GASES BY EFFECTING A KNOWN DISPLACEMENT

This application is a division of application Ser. No. 112,117 which was filed on Oct. 26, 1987, now U.S. Pat. No. 4,873,971, which in turn is a continuation-in-part of application Ser. No. 783,121 which was filed on Oct. 2, 1985 and is now U.S. Pat. No. 4,705,034.

BACKGROUND OF THE INVENTION

This invention relates generally to methods and apparatus for administering oxygen and other respirating gases to a patient.

More particularly, this invention relates to methods and means for administering oxygen or other gases to a patient on an intermittent, respiration controlled, basis.

It has become common medical practice to treat patients suffering from advanced stages of chronic obstructive pulmonary diseases by administration of oxygen. Such pulmonary diseases, including chronic bronchitis, emphysema and severe asthma, are one of the fastest rising causes of death in the United States affecting probably more than ten mil It is estimated that more than 500,000 people in the United States either are routinely receiving oxygen therapy or could benefit from it. Much of this rather expensive treatment is funded by Medicare.

The devices which commonly have been used to deliver oxygen to a patient meter the oxygen flow at a fixed rate and deliver a constant stream of oxygen to the patient. Oxygen is received by the patient either through a mask which is placed over the nose and mouth or through a cannula which terminates in nares inserted into the patient's nostrils.

It has long been recognized that providing a constant flow of oxygen to a patient results in the waste of a substantial proportion of the oxygen supply. The normal breathing cycle consists of an inhalation, an exhalation longer in duration than the inhalation, and then a pause before the next cycle. Oxygen supplied to a patient during the exhalation and pause phases of the respiratory cycle is totally wasted. Devices have been developed to conserve oxygen by regulating the oxygen flow, turning it on and off, in response to the respiratory cycle. Typical of such devices are those of Myers, U.S. Pat. No. 4,054,133, and Mon, U.S. Pat. No. 4,381,002. Each of these patents disclose devices which sense inhalation and exhalation pressures in the nasal cavity of a patient and converts those sensed pressure differentials to signals which control the flow of oxygen to a patient. Typically, oxygen flow is started upon the sensing of a negative pressure relative to atmospheric indicating the start of an inspiration period. Oxygen flow is then stopped at a second signal produced by the sensing of a positive pressure relative to atmospheric indicating the start of the expiration period.

More recently Dr. Gerald Durkan clinically observed that only the oxygen supplied during the initial part of an inspiration period was efficiently absorbed by a patient. It is that first inspired portion of oxygen which reaches the alveoli while oxygen supplied during the latter part of an inspiration period remains in non-absorbing areas such as the pharynx, trachea and bronchial tubes. Durkin concluded that supplying oxygen at a high rate, beginning at the start of inspiration but lasting only for a small portion of the inspiration period offered economic and physiologic advantages over those prior techniques which supplied oxygen during the entire inspiration period.

As a result of his observations, Durkan developed a respirator system known as the Demand Oxygen Controller which is disclosed in U.S. Pat. No. 4,457,303. That respirator system uses a fluidic laminar proportional amplifier to sense the start of an inspiration period. Oxygen flow to a patient is immediately started in response to the sensed inspiration. Timing means, also started in response to the sensed inspiration, stop the oxygen flow after a preset period of time which is shorter than is the inspiration period. As a result, oxygen is supplied to a patient only during the effective, early stages of an inspiration resulting in an oxygen savings of as much as 70% as compared to a continuous flow administration.

All of these prior art techniques have one property in common. All determine or control the volume of oxygen (or other respirating gas) delivered to the patient over a respiratory cycle by controlling both the rate at which oxygen is allowed to flow and the time or duration of oxygen flow for each respiratory cycle. Both Myers and Mon teach the starting of oxygen flow upon sensing the beginning of an inspiration and the stopping of oxygen flow upon the sensing of an expiration. Durkan teaches the starting of oxygen flow upon sensing the beginning of an inspiration and stops oxygen flow at the end of a time period which is independent from, and shorter than, the inspiration period.

Those prior art devices which connect a rate metered supply of oxygen to a cannula for a predetermined time to effect the desired dose delivery all have the disadvantage that both the rate and duration of flow must be precisely controlled if the dose is to be accurately measured and dispensed. Because of the small quantities of oxygen required per dose (typically about 33 cc measured at standard temperature and pressure), it is difficult and expensive on a production basis to provide for the degree of accuracy of flow rate and of timing required to ensure a safe dose efficiently delivered for each breath. An improved and simplified way to dispense an oxygen dose in synchronization with a patient's respiratory cycle provides clear advantages in this art.

SUMMARY OF THE INVENTION

A method and apparatus for administering oxygen or other medical gases to a patient in sychronization with the respiratory cycle of the patient operates by generating a signal in response to the onset of an inhalation and immediately dispenses a premeasured volume of the oxygen or other gas by effecting a known displacement. Displacing means suitable for use include a cylinder containing a spring loaded piston which is filled from a pressurized gas supply forcing the piston back to a stop set to control the volume. Other displacing means include a pressurized, adjustable volume which is blown down into the cannula for dose delivery.

Hence, it is an object of this invention to provide a method and means to supply measured doses of respirating gases to a patient during the early stages of an inspiration and dispensing a premeasured gas volume by effecting a known displacement.

It is another object of this invention to provide a simplified respirator apparatus which does not employ timing means to control dose volume.

Other objects of this invention will be apparent from the following description of certain embodiments of the invention.

DESCRIPTION OF THE DRAWING

Specific embodiments of the invention are illustrated in the drawing in which:

FIG. 6-A shows another control circuit especially useful with the embodiments of FIGS. 2 and 4;

DESCRIPTION AND DISCUSSION OF THE INVENTION

Figure 1:
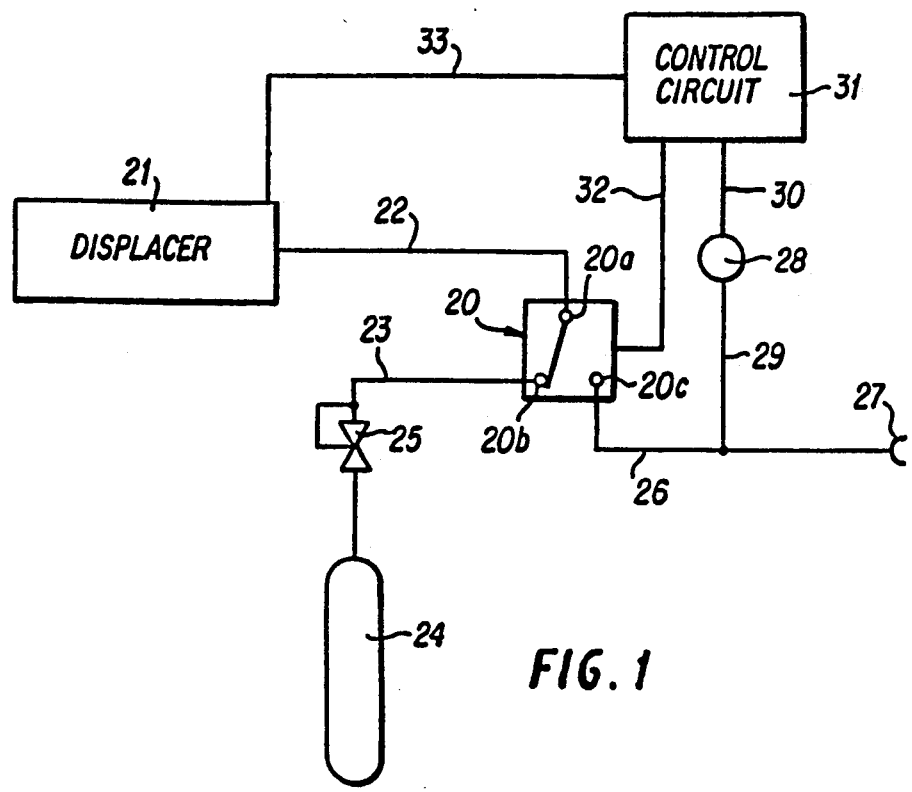
FIG. 1 is a schematic diagram showing generally the gas supply apparatus of this invention.

Various embodiments of this invention will be described and discussed in detail with reference to the drawing figures in which like reference numerals refer to the same component or part illustrated in different figures.

Referring first to FIG. 1, there is shown in its simplist schematic form the gas supply apparatus of this invention. The device comprises a three-way valve means 20 having its common port 20a connected to a displacer or containment means 21 by way of a conduit 22. One of the two option ports 20b is connected by line 23 to a supply of respirating gas, typically oxygen, 24. Gas delivered through line 23 is maintained at a relatively constant pressure, typically about 20 psig, by means of pressure regulator 25. The other option port, 20c, is connected to a cannula or other delivery system 26 which terminates in nares or mask 27.

In use, with valve 20 in the position shown, oxygen from source 24 at the pressure controlled by regulator 25 flows directly to displacer 21. There it effects a preset displacement equal to a unit dose, for one breath, of oxygen measured at standard conditions. Displacer 21 thus performs two distinct functions. First, it premeters or measures a quantity or mass of gas equal to the prescribed unit dose for one breath. Second, it temporarily parks or stores that premetered quantity, or unit dose and then releases that stored unit dose in synchronization with the onset or start of the patient's inhalation. By first premetering and then temporarily storing each single or unit dose of gas, the source of respirating gas is always isolated from direct communication with the patient by the displacer which provides significant safety features not attainable with conventional devices.

Displacer 21 may be of two distinct types, each type operating in a different mode but accomplishing essentially the same result. In one type of displacer, gas is mechanically pushed, or displaced from, a known volume through action of a piston or similar means. In a second type of displacer which is advantageous to use at high source pressures, there is provided a fixed volume reservoir which is filled or loaded at source pressure and which discharges a unit dose to the patient by releasing, or blowing down, the pressurized gas within the reservoir to essentially atmospheric pressure.

It is conventional to express a unit dose of respirating gas in terms of a gas volume at normal temperature and pressure. Gas dispensing means of this general type typically operate at ordinary room temperature so gas volume changes due to temperature variations may be safely ignored. Hence, the operating volume of both types of displacer or containment means 21 is dependent upon the pressure of the gas source. For example, if the volume of oxygen prescribed for one breath or unit dose is 33 cc (approximately equal to a continuous rate of 2 liters per minute), then the required displacement volume of the first described type of displacer at a source pressure of 20 psig would be about 14 cc. Were the second type of described displacer (the embodiment of FIG. 4) to be used, then at a source pressure of 20 psig, the reservoir volume required would be about 24 cc. In either type of displacer, a change in the prescribed unit dose of respirating gas is accommodated by changing the displaced volume (or blowdown volume) in ways which will later be described. It is, of course, also possible to control, or change, the unit dose by changing the source pressure but that dose size control method is less preferred.

Each dose of oxygen must be delivered in synchronization with the patient's inspiratory cycle. To accomplish that synchronous delivery necessarily requires an extremely sensitive and fast responding sensor 28 which is operably connected to cannula 26 by means of line 29 so that, for example, it may monitor and respond to slight changes of pressure occurring in the nasal cavity of the patient. Exemplary sensors meeting those requirements and known in the prior art include a spring-loaded diaphragm sensor as shown by Myers in U.S. Pat. No. 4,054,133 and fluidic devices employing laminar proportional amplifiers as shown by Mon in U.S. Pat. No. 4,381,002 and Durkan in U.S. Pat. No. 4,457,303. A thermistor-type sensor responsive to directional gas flow may also find use in the devices of this invention. Also, a sensitive pressure-to-electric switch, such as the Microswitch, Series 160, may be employed.

Sensor 28 is arranged to produce a signal upon detection of the beginning of an inhalation by the patient. The signal, which may be electrical or pneumatic, is transmitted via means 30 to control circuit 31. Control circuit 31, responding to the signal from sensor 28, activates triggering means 32 causing valve 20 to move to its other position connecting port 20a with port 20c. In this position, oxygen source 24 is isolated from the remainder of the system and the unit dose of oxygen in displacer 21 surges through line 22 and valve 20 into cannula 26 and thence to the patient. A signal 33 is produced by displacer 21 upon completion of the delivery of a unit dose of oxygen causing control circuit 31 to reset valve 20 to its original position thus beginning the cycle anew.

Figure 2:
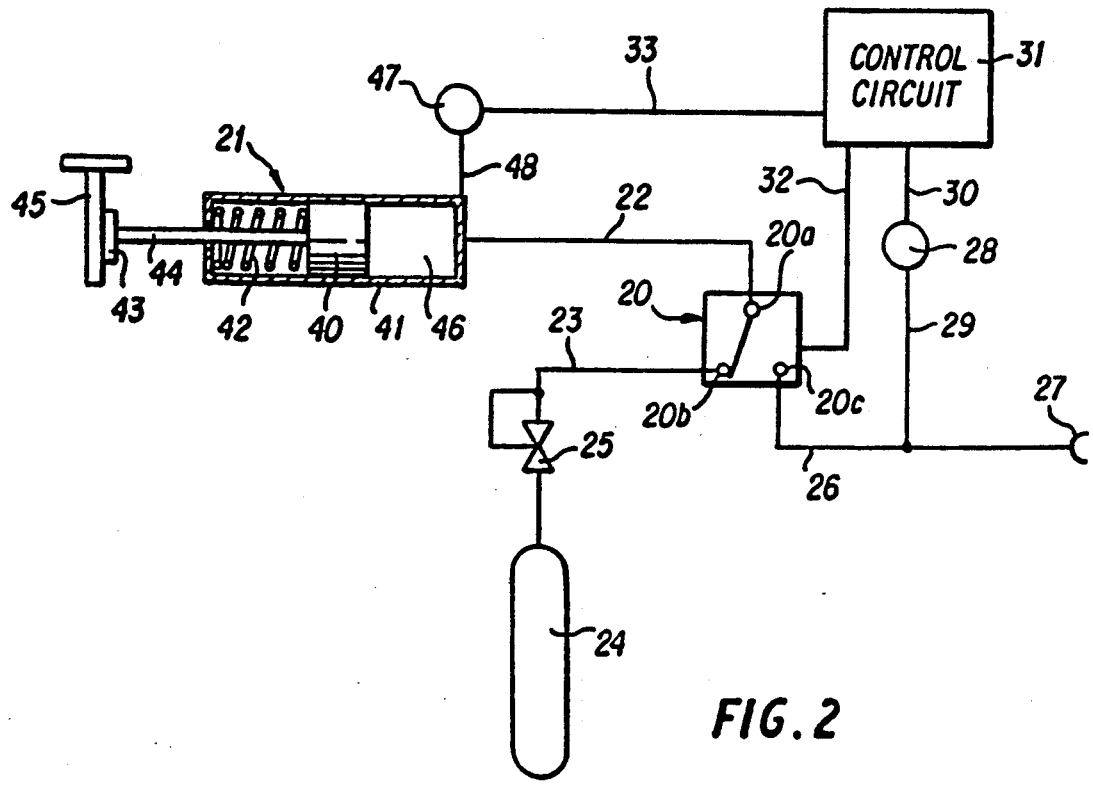
FIG. 2 illustrates in partial section one embodiment of a displacement dispenser for use with the gas supply apparatus.

FIG. 2 illustrates the gas supply apparatus of FIG. 1 which utilizes a piston-type displacer 21. In this embodiment, displacer 21 comprises a piston 40 operating within a cylinder 41. When valve 20 is in the position illustrated, with port 20a connected to port 20b, oxygen from source 24 enters the end of cylinder 41 through line 22 forcing piston 40 back against spring 42 until the end 43 of piston rod 44 engages stop 45. Stop 45, in a preferred embodiment, is adjustable so as to allow varying the volume 46 (and hence the unit dose of oxygen administered per breath) within cylinder 41 when the piston 40 is at the limit of its travel.

So long as valve 20 is in the position shown, pressure exerted upon the head of piston 40 by the gas from source 24 maintains spring 42 under compression and the piston rod end 43 firmly against stop 45. Upon detection of the start of an inhalation by the patient, sensor 28 transmits a signal via 30 to control circuit 31 which in turn causes valve 20 to move to its other position with valve port 20a connected to port 20c. Spring 42 then forces the piston 40 forward to the end of cylinder 41 causing the gas within the cylinder to surge through line 22 and valve 20 into cannula 26 and thence to the patient. A sensor 47, which may comprise a differential pressure switch, a magnetic reed switch or a microswitch, is operably arranged through means 48 to detect the completion of the piston travel and to transmit a signal 33 to control circuit 31. Thereupon, valve 20 resets to its refill position and the fixed volume 46 is refilled for the next cycle.

Figure 3:
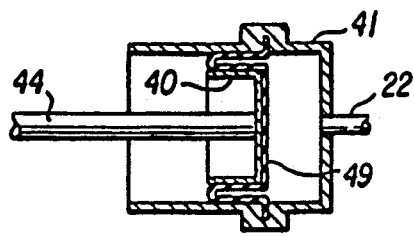
FIG. 3 illustrates a rolling diaphragm type of piston displacing means preferred in certain embodiments of this invention.

One particularly preferred piston and cylinder arrangement for use as the displacer 21 of this invention is illustrated in FIG. 3. This device is commercially available under the tradename Bellofram Rolling Diaphram and is described in detail in U.S. Pat. Nos. 3,137,215 and 3,373,236. As shown in FIG. 3, the device includes a diaphragm 49 which is formed in the shape of a truncated cone with its center fastened to the head of piston 40 and its outer flange clamped to cylinder 41. Diaphragm 49 alternately rolls and unrolls on the skirt of piston 40 and the wall of cylinder 41 as the piston travels back and forth. The rolling action of diaphragm 49 eliminates sliding contact and breakaway friction. The diaphragm arrangement forms a complete seal preventing blow-by leakage and pressure loss and requires no lubrication of any kind. These features make the device highly advantageous to use in the dispensing of respirating gases to a patient.

Figure 4:
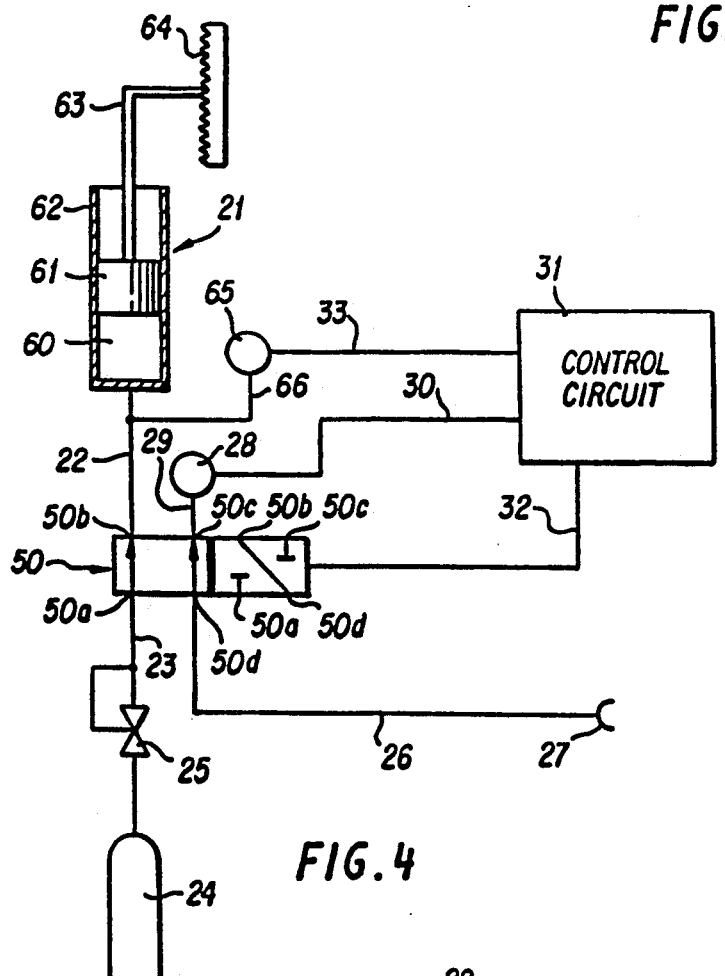
FIG. 4 is a diagram in partial section of a fixed volume, but adjustable, gas dispensing means.

FIG. 4 illustrates another embodiment of this invention which utilizes a fixed volume reservoir filled or loaded at source pressure and arranged to discharge a unit dose to a patient by releasing, or blowing down, the pressurized gas within the reservoir to essentially atmospheric pressure. It is especially useful with higher pressure oxygen sources such as those central systems having distribution lines to multiple locations as in many hospitals and other health care facilities. Those central systems typically maintain an oxygen pressure of about 50 psig in the distribution lines. This embodiment employs a two-position valve 50 having four ports 50a, 50b, 50c and 50d. In the valve position shown, the gas source 24 is connected through valve ports 50a and 50b and line 22 directly to a fixed volume chamber 60 within displacer 21. The displacer unit or containment means in this embodiment may comprise a piston with a rolling diaphragm as is illustrated in FIG. 3. Unlike the embodiment of FIG. 2, however, piston 61 within cylinder 62 remains stationary during operation of the gas supply apparatus. Provision is made for changing, or setting, the volume 60 (in order to fix a unit dose of oxygen dispensed per breath) by moving piston 61 up and down through connecting rod 63 which is adapted to lock into adjustment rack 64 at the desired volume or unit dose position.

While valve 50 is in the first, or fill, position sensor 28 is connected via line 29 and valve ports 50c and 50d to the cannula 26. Upon the detection of the start of an inhalation, sensor 28 produces a signal which is transmitted to control circuit 31 by means 30. That signal may be either pneumatic or electrical depending upon the type of device employed as the sensor 28. The signal from sensor 28 causes control circuit 31 to actuate valve 50 through means 32 and so change the valve to its other position. In this other position, valve port 50b is connected to port 50d while ports 50a and 50c are isolated from the system. Pressurized gas in fixed volume chamber 60 thus has an open flow path via line 22, through valve 50 to cannula 26 and thence to the patient causing the pressure within chamber 60 to drop rapidly to essentially atmospheric. A differential pressure switch, or other suitable sensor, 65 is connected to chamber 60 through conduit 66 and transmits a signal via means 33 to the control circuit 31 upon depletion of the pressure within chamber 60. This signal causes the control circuit 31 to reset valve 50 back to its original, or refill, position thus starting a new cycle The valving arrangement depicted in this embodiment isolates sensor 28 from the pressure surge which occurs as oxygen flows from chamber 60 to the patient. This arrangement is advantageous in those cases wherein the construction of sensor 28 might be damaged by sudden positive over pressures. This valving arrangement may, of course, also be used in the embodiment depicted in FIG. 2. In addition to simplicity, the compact size of the device of this embodiment may be appreciated by calculation of the volume 60 required to deliver a unit dose of 33 cc of oxygen measured at standard conditions. At a system pressure of 50 psig, volume 60 would be set at approximately 10 cc to deliver 33 cc of oxygen measured at atmospheric pressure.

Figure 5:
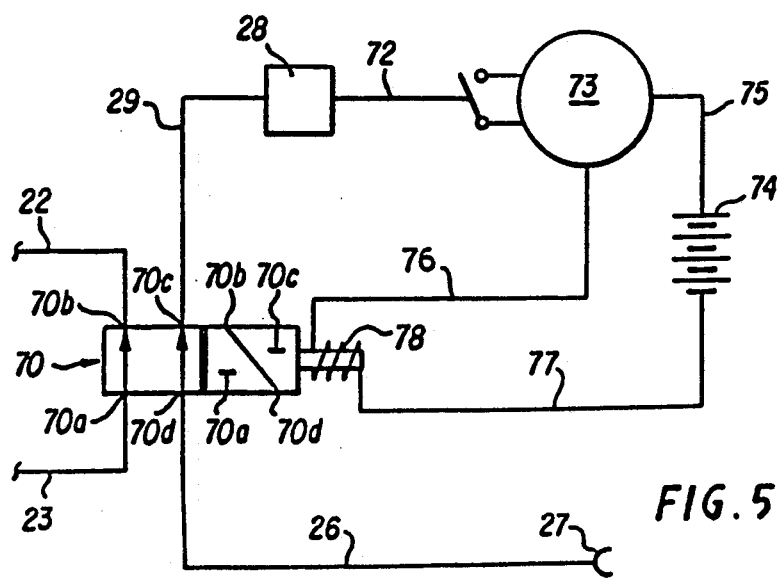
FIG. 5 schematically depicts one specific control circuit preferred for use with certain embodiments of this invention.

Control circuit 31 has been described in functional terms in relation to the embodiments shown in FIGS. 1, 2 and 4. FIG. 5 illustrates details of a control circuit especially adapted to the embodiment of FIG. 4 but also appropriate for use with the embodiment of FIG. 2. There is shown a four-way, two position valve 70 in the refill position wherein line 23 communicates with a source of respirating gas via port 70a and line 22 leads to a displacer via port 70b. Cannula 26 is connected to line 29 and sensor 28 through ports 70c and 70d. Sensor 28 may be of any type having adequate sensitivity to detect the onset of inhalation. It may, for example, be a very sensitive pressure switch, a fluidic amplifier or a thermistor which reacts to flow. Sensor 28, upon detection of the onset of an inhalation, produces a trigger signal 72 which activates interval timer 73. Interval timer 73 is of the type commonly called a one-shot timer or a time delay relay which, upon receiving the trigger signal, initiates a timed cycle of power from power supply 74. This cycle of power, traveling through conductors 75, 76 and 77, activates the solenoid coil 78 of valve 70 causing it to move to its other position wherein port 70b is connected to port 70d and wherein ports 70a and 70c are isolated from the system. At the end of the cycle period, the electric power pulse stops, valve 70 returns to its original, or reset, position, and the interval timer 73 resets to an "off" position until the next trigger signal. The exact duration of the electric power pulse produced by interval timer 73 is not important so long as it is long enough to permit complete delivery of the stored pulse volume in the displacer chamber and short enough to allow sufficient time for the metering chamber (volume 60 of FIG. 4) to refill in time for the next cycle. A range of times from about ⅜ to ¾ of a second is generally appropriate with a period of ½ second being a good design target. It is important to note that dose volume is, within wide limits, completely independent of electric pulse duration; the volume of a unit dose being directly determined by effecting a known displacement.

The control circuit of FIG. 5 may also be modified to employ pneumatic means, rather than the illustrated solenoid coil 78, to cause valve 70 to move from one position to the other. In this embodiment, gas stored under pressure in displacer 21 may be used as the motive fluid to power the valve actuator. Gas used to power valve movement need not be wasted but may be discharged into cannula 26 for use by the patient.

Figure 6:
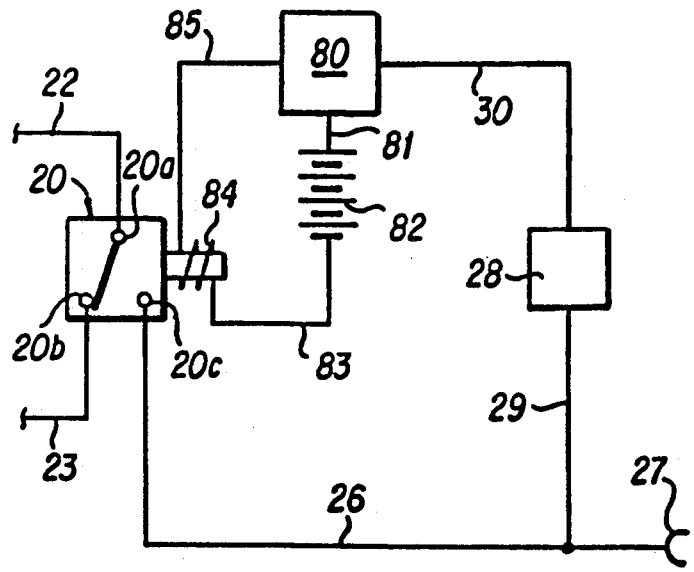
FIG. 6 illustrates another control circuit suitable for other embodiments of this invention.
Figure 6A:
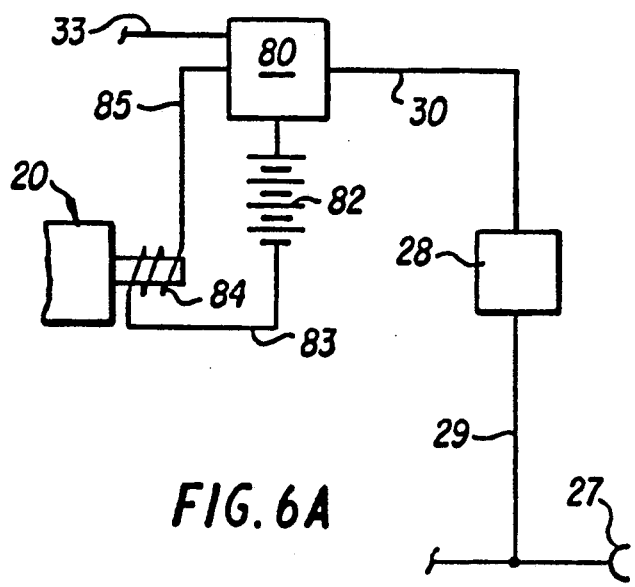

FIG. 6 illustrates another control circuit which is particularly adapted for use with the embodiment of FIG. 2. The circuit includes a flip-flop relay 80 in series connection via conductor 81 with a power supply 82, second conductor 83, valve solenoid coil 84 and third conductor 85. Sensor 28, in this embodiment, detects the onset of both an inhalation and an exhalation and transmits a trigger signal to relay 80 upon the occurrence of each event. As shown in the Figure, valve 20 is in the refill position wherein the displacer is in direct communication with a source of respirating gas. Upon receiving a signal representative of the onset of an inhalation from sensor 28, flip-flop relay 80 will, through activation of solenoid coil 84, cause valve 20 to move to its other position. The valve 20 in its other position puts the displacer via line 22 into direct communication with cannula 26. Valve 20 remains in this other position until relay 80 receives from sensor 28 a second signal representative of the onset of an exhalation. At that time, relay 80 causes valve 20 to return to its original, or refill, position. The onset of an inhalation produces a small negative pressure relative to ambient while the onset of an exhalation produces a slight positive pressure relative to ambient. Thus, sensor 28 can be arranged to produce signals of different polarity, corresponding to negative and positive pressures, which ensures that flip-flop relay 80 will cause valve 20 to remain in proper synchronization with the breathing cycle of the patient.

FIG. 6-A shows yet another variation of control circuit 31 which is adaptable for use with the embodiments of both FIGS. 2 and 4. This embodiment uses a flip-flop relay 80, as does the circuit of FIG. 6, but sensor 28 is arranged to produce a signal only upon the onset of an inhalation. Upon receiving a signal from sensor 28, relay 80 activates the solenoid coil 84 of the valve means to that valve position wherein a unit dose of oxygen or other respirating gas is delivered from the displacer to the cannula. A signal 33 is received by relay 80 from the displacer (as was described in relation to FIGS. 2 and 4) when the piston has reached the limit of its travel (FIG. 2) or when the pressure within the fixed volume chamber has depleted to atmospheric (FIG. 4). Signal 33 causes relay 80 (and coil 84) to flip to its other, or refill, position thus completing a cycle.

Figure 7:
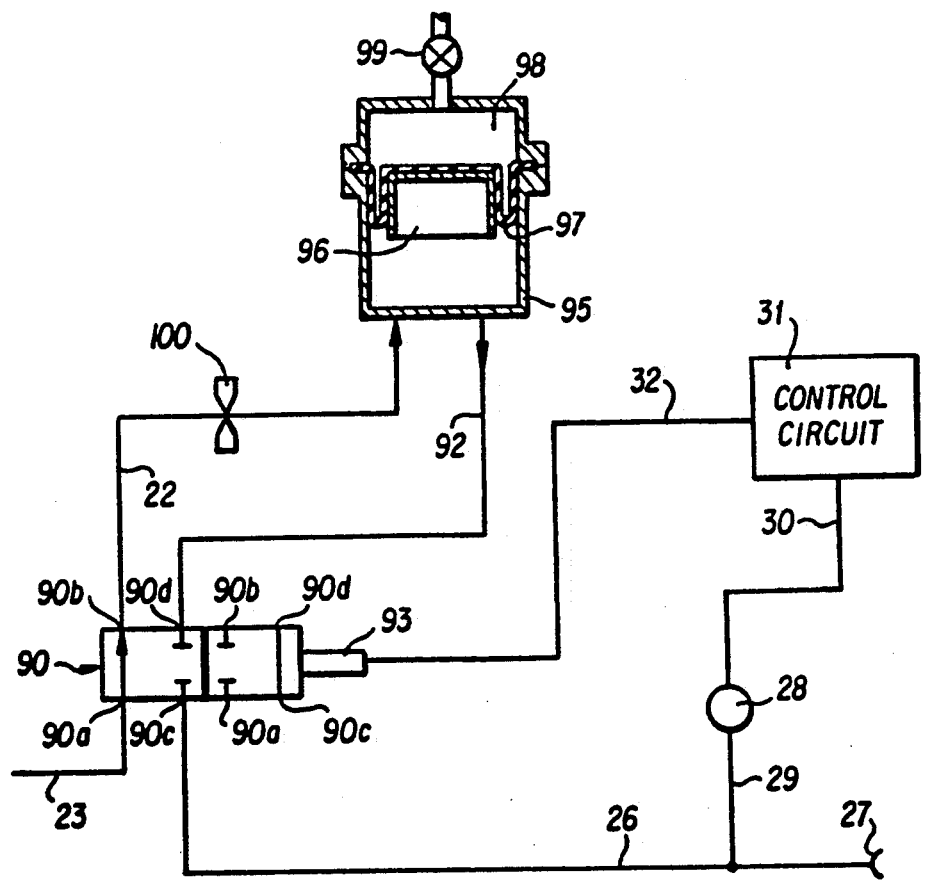
FIG. 7 depicts an alternative embodiment of this invention including means to prevent over-oxygenation in the event of hyperventilation.

FIG. 7 depicts another embodiment of the gas supply apparatus of this invention which includes provision for preventing over-oxygenation in the event that there is hyperventilation by the patient. This embodiment employs a two-position valve 90 having four ports 90a, 90b, 90c and 90d. In the valve position illustrated, gas flows from a source (not shown) by way of line 23 through valve ports 90a and 90b and line 22 to the interior of displacement means 95. Containment means 95 may conveniently be a piston 96 with a rolling diaphragm 97 disposed within a cylinder as is illustrated in FIG. 3. The piston may be arranged to reciprocate back and forth as in the embodiment of FIG. 2 or may remain stationary during operation as in the embodiment of FIG. 4. In that embodiment employing reciprocation of piston 96, the resilient restoring means may be provided by a pneumatic chamber 98 rather than the mechanical spring means shown in FIG. 2. The magnitude of the pneumatic restoring force may be set at any desired level through adjustment of the gas pressure within chamber 98 by adding gas to or withdrawing gas from chamber 98 by way of valve means 99.

There is also provided a flow rate limiting means 100 located in the gas supply line to the displacement means 95. In this embodiment, means 100 is preferably located in line 22 between valve 90 and displacement means 95 while in the embodiments of FIGS. 2 and 4, means 100 is preferably located in line 23 upstream of the valve means. Flow rate limiting means 100 may conveniently comprise an orifice sized so that the maximum flow rate of oxygen through the orifice is less than that which will produce over-oxygenation of the patient if delivered on a continuous basis. Thus, no matter how fast the patient breathes, there will be an upper limit to the amount of oxygen which will be delivered to the patient per unit of time.

There is also provided another line 92 communicating between the interior of containment means 95 and port 90d of valve 90. The opposite valve port, 90c, is connected to cannula 26 which terminates in nares (or mask) 27. In the valve position shown, line 92 is isolated from cannula 26 by valve 90. Sensor 28 may be connected by way of line 29 to cannula 26. Upon detection of the start of an inhalation, sensor 28 produces a signal which is transmitted to control means 31 by means 30. Control means 31, in turn, causes actuator 93 to change the valve to its other position. In this other position, line 22 is isolated from source line 23 while line 92 is connected to cannula 26 releasing the dose of gas within containment means 95 and allowing that dose to flow through the cannula for breathing by the patient.

Figure 8:
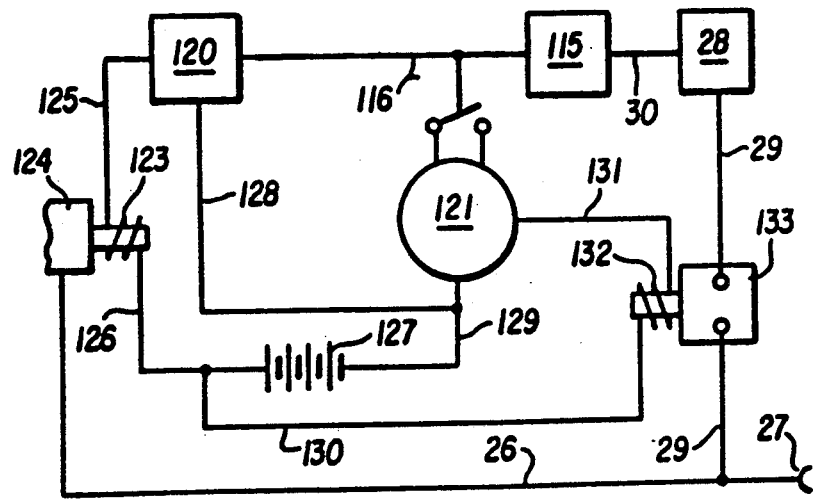
FIG. 8 schematically depicts another control circuit embodiment useful with the dispensing means of this invention.

Turning now to FIG. 8, there is shown a control circuit which may be used with any or all of the containment means embodiments of this invention. In the circuit shown, sensor 28 is arranged to produce a signal only upon the detection of the onset of an inhalation. That signal 30 is transmitted to a counting and controlling means 115. Means 115 is arranged to count signals produced by sensor 28 and, after receiving a preselected number of signals from sensor 28, to transmit an activating signal 116 to a relay 120 and to a time delay relay 121. Activating signal 116 triggers relay 120 activating solenoid coil 123 of flow control valve 124 by way of the circuit comprising conductors 125 and 126, power supply 127 and conductors 128 and 129. Flow control valve 124 may be a three-port, two-position valve as in FIG. 2 or may be a four-port, two-position valve as shown in FIGS. 4 and 7, or functional equivalents thereof. Signal 116 also activates interval timer 121 which, upon receiving the signals initiates a timed cycle of power from power supply 127 by way of conductors 129, 130 and 131 causing solenoid coil 132 to change the position of valve 133. Valve 133 is a simple two-way isolating valve which is inserted into line 29 connecting sensor 28 with cannula 26. Valve 133 is arranged to be in the closed position while solenoid coil 132 is activated by interval timer 121. The power pulse produced by interval timer 121 is long enough, typically about ½ second, to shield the sensor 28 from the rush of respirating gas released upon the onset of an inhalation by movement of flow control valve 124. At the end of timed interval, solenoid 132 is de-energized and valve 133 returns to the open position re-connecting sensor 28 with cannula 26.

Incorporation of counting and controlling means 115 into the circuit allows greater flexibility in the dispensing of gas doses to a patient. Means 115 may be set so as to produce a signal 116, and thereby to deliver a prescribed single dose quantity of supplemental oxygen, on each inhalation signal, on every second inhalation signal, on every third inhalation signal, and so forth. In this way maximum flexibility in the dispensing of supplemental oxygen to a patient may be attained.

In each and all of the embodiments of this invention, the cannula, or other gas delivery means to the patient, is never in direct communication with the source of the respirating gas. Prior art devices can be generally characterized is providing direct communication, or an open flow path, between the source of the respirating gas and the patient while gas delivery is in progress. Pre-metering and temporarily storing each unit dose of respirating gas, as the devices of this invention do, inherently provides safety features not present in conventional gas delivery systems.

As has been described in relation to the various embodiments, this invention provides both an improved and a simplified way to dispense gases to a patient by effecting a known displacement. The duration of delivery can still be relatively short so as to improve the patient's utilization of the dose but the duration of delivery does not need to be precisely controlled. In fact, by using the method and apparatus of this invention, the time of delivery will tend to be non-linear with variations in prescribed dosages.

Other embodiments of and uses for this invention will be apparent to those skilled in the art without departing from the spirit and scope of the following claims.

I claim:

1. A device for supplying premeasured doses of respirating gas to a patient in synchronization with the respiratory cycle of the patient comprising:
a source of respirating gas at relatively high pressure;
containment means having a volume sized to measure a prescribed single dose quantity of said respirating gas at source pressure and to temporarily store said measured dose;
means for sensing the onset of inhalations of the patient and for producing signals in response to said sensing;
valve means arranged to move between a first position and a second position in response to said produced signals, said valve means comprising a three-way valve having two option ports and a common port;
cannula means;
first gas flow routing means for connecting said gas source to one of said option ports;
second gas flow routing means for connecting said containment means to said common port;
third gas flow routing means for connecting one end of said cannula means to the other of said option ports; and
means connected to the other end of said cannula means and adapted for communication with the nasal cavity of the patient, said valve means in its first position connecting said first gas flow routing means to said second gas flow routing means and placing said gas source in communication with said containment means thereby filling said containment means with respirating gas at source pressure, said valve means in its second position connecting said second gas flow routing means to said third gas flow routing means and placing said containment means in communication with said means connected to the other end of the cannula means thereby releasing said measured dose quantity of respirating gas from said containment means and conveying said gas dose to the patient.

2. A device for supplying premeasured doses of respirating gas to a patient in synchronization with the respiratory cycle of the patient comprising:
a source of respirating gas at relatively high pressure;
containment means having a volume sized to measure a prescribed single dose quantity of said respirating gas at source pressure and to temporarily store said measured dose;
means for sensing the onset of inhalations of the patient and for producing signals in response to said sensing, said means for sensing producing a first electrical signal in response to said sensing;
solenoid-operated valve means arranged to move between a first position and a second position;
cannula means adapted for communication with the nasal cavity of the patient;
first gas flow routing means for connecting said gas source to said valve means;
second gas flow routing means for connecting said valve means to said containment means;
third gas flow routing means for connecting said valve means to said cannula means;
a flip-flop relay having a power supply associated therewith, said relay activated by said first electrical signal to thereby cause said relay and said solenoid to move said valve means from its first said position to its said second position, said valve means in its first position connecting said first gas flow routing means to said second gas flow routing means and placing said gas source in communication with said containment means thereby filling said containment means with respirating gas at source pressure, said valve means in its second position connecting said second gas flow routing means to said third gas flow routing means and placing said containment means in communication with said cannula means thereby releasing said measured dose quantity of respirating gas from said containment means and conveying said gas dose to the patient.

3. The device of claim 2 wherein said means for sensing comprises a sensor, wherein said sensor produces a second electrical signal representative of the onset of an exhalation, said second electrical signal being transmitted to said flip-flop relay causing said relay and said solenoid to move said valve means from its second said position back to its first said position whereupon said containment means is refilled from said gas source.

4. The device of claim 2 wherein said means for sensing comprises a sensor said sensor arranged to produce an electrical signal only upon the onset of an inhalation, wherein said containment means is arranged to produce a different electrical signal upon release of said gas dose, and wherein said different electrical signal is transmitted to said relay causing said relay and said solenoid to move said valve from its second said position back to its first said position whereupon said containment means is refilled from said gas source.

5. A device for supplying premeasured doses of respirating gas to a patient in synchronization with the respiratory cycle of the patient comprising:

a source of respirating gas at relatively high pressure;

containment means having a volume sized to measure a prescribed single dose quantity of said respirating gas at source pressure and to temporarily store said measured dose;

means for sensing the onset of inhalations of the patient and for producing signals in response to said sensing;

solenoid-operated valve means arranged to move between a first position and a second position;

cannula means adapted for communication with the nasal cavity of the patient;

first gas flow routing means for connecting said gas source to said valve means;

second gas flow routing means for connecting said valve means to said containment means;

third gas flow routing means for connecting said valve means to said cannula means; and an interval timer and means to transmit a signal produced by said sensing means to said timer; said interval timer arranged to activate the solenoid of said valve means and to thereby cause said valve means to move from its first position to its second position for the duration of the timed interval, said valve means in its first position connecting said first gas flow routing means to said second gas flow routing means and placing said gas source in communication with said containment means thereby filling said containment means with respirating gas at source pressure, said valve means in its second position connecting said second gas flow routing means to said third gas flow routing means and placing said containment means in communication with said cannula means thereby releasing said measured dose quantity of respirating gas from said containment means and conveying said gas dose to the patient, said timed interval being sufficiently long to allow release of said gas dose from said containment means.

6. A device for supplying premeasured doses of respirating gas to a patient in synchronization with the respiratory cycle of the patient comprising:

a source of respirating gas at relatively high pressure;

containment means having a volume sized to measure a single dose quantity of respirating gas at source pressure and to temporarily store said measured dose, said containment means comprising a cylinder having a piston which is movable therein;

means for sensing the onset of inhalations of the patient and for producing signals in response to said sensing;

valve means arranged to move between a first position and a second position in response to said produced signals;

cannula means adapted for communication with the nasal cavity of the patient;

first gas flow routing means for connecting said gas source to said valve means;

second gas flow routing means for connecting said valve means to said containment means;

third gas flow routing means for connecting said valve means to said cannula means; and means arranged to mechanically move said piston for a fixed distance within said cylinder upon movement of said valve means from its first position to its second position, said valve means in its first position connecting said first gas flow routing means to said second gas flow routing means and placing said gas source in communication with the interior of said cylinder thereby filling said cylinder with respirating gas at source pressure, said valve means in its second position connecting said second gas flow routing means to said third gas flow routing means and placing the interior of said cylinder in communication with said cannula means thereby delivering said measured dose of respirating gas to the patient during the early stage of a sensed inhalation.

7. The device of claim 6 wherein said piston has a head an skirt, and further includes a diaphragm in the shape of a truncated cone having a center and an outer flange sealingly clamped to said cylinder, wherein said center is fastened to the head of said piston; said diaphragm alternately rolling and unrolling on the skirt of said piston and a wall of said cylinder as the piston travels back and forth.

8. The device of claim 6 wherein said means to move said piston comprises resilient restoring means arranged to be compressed by the source pressure of respirating gas on said piston.

9. The device of claim 8 wherein said resilient restoring means comprises a mechanical spring means.

10. The device of claim 8 wherein said resilient restoring means comprises a closed chamber having gas therein.

11. The device of claim 6 including stop means adapted to define said fixed distance through which the piston is allowed to move within said cylinder, the position of said stop means being adjustable so as to allow delivery of different prescribed doses of respirating gas by varying the volume displaced by one stroke of said piston within the cylinder.

12. A device for supplying premeasured doses of respirating gas to a patient in synchronization with the respiratory cycle of the patient comprising:

a source of respirating gas at relatively high pressure;

containment means comprising a fixed volume reservoir arranged to temporarily store a volume of gas and sized such that a prescribed dose of respirating gas is discharged by blowing down said reservoir from source pressure to atmospheric pressure;

means for sensing the onset of inhalations of the patient and for producing signals in response to said sensing;

valve means arranged to move between a first position and a second position in response to said produced signals;

cannula means adapted for communication with the nasal cavity of the patient;

first gas flow routing means for connecting said gas source to said valve means;

second gas flow routing means for connecting said valve means to said containment means;

third gas flow routing means for connecting said valve means to said cannula means;

said valve means in its first position connecting said first gas flow routing means to said second gas flow routing means and placing said gas source in communication with said reservoir thereby filling said reservoir with respirating gas at source pressure, said valve means in its second position connecting said second gas flow routing means to said third gas flow routing means and placing said reservoir in communication with said cannula means thereby allowing said reservoir to blow down from source pressure at atmospheric pressure to release a measured dose quantity of respirating gas and convey said gas dose to the patient.

13. The device of claim 12 wherein said reservoir comprises a piston disposed within a cylinder, said piston adapted to be positioned at one of several fixed locations within said cylinder, each of said fixed locations providing a cylinder volume holding a prescribed dose quantity of respirating gas.

14. The device of claim 13 wherein said piston includes a diaphragm in the shape of a truncated cone with its center fastened to the head of said piston and its outer flange sealingly attached within said cylinder in a manner which allows said diaphragm to roll and unroll on the skirt of said piston and the wall of said cylinder as the piston is positioned at different locations within the cylinder.

* * * * *